United States Patent
Butters et al.

(10) Patent No.: US 10,107,853 B2
(45) Date of Patent: Oct. 23, 2018

(54) APPARATUS AND METHOD FOR INSPECTING PCB-MOUNTED INTEGRATED CIRCUITS

(75) Inventors: Simon Butters, Dorset (GB); David Hall, Winkleigh (GB)

(73) Assignee: TWENTY TWENTY VISION LIMITED, Dorset (GB)

( * ) Notice: Subject to any disclaimer, the term of this patent is extended or adjusted under 35 U.S.C. 154(b) by 974 days.

(21) Appl. No.: 13/988,468

(22) PCT Filed: Nov. 18, 2011

(86) PCT No.: PCT/EP2011/070504
§ 371 (c)(1),
(2), (4) Date: Sep. 21, 2013

(87) PCT Pub. No.: WO2012/066139
PCT Pub. Date: May 24, 2012

(65) Prior Publication Data
US 2014/0043033 A1 Feb. 13, 2014

(30) Foreign Application Priority Data
Nov. 18, 2010 (GB) .................................. 1019537.8

(51) Int. Cl.
G01R 31/311 (2006.01)
G01R 31/265 (2006.01)
H05K 13/08 (2006.01)

(52) U.S. Cl.
CPC ......... *G01R 31/2656* (2013.01); *H05K 13/08* (2013.01)

(58) Field of Classification Search
CPC .............................. G01R 31/2656; H05K 13/08
(Continued)

(56) References Cited

U.S. PATENT DOCUMENTS 4,165,178 A * 8/1979 Coumo, Jr. ............ G01B 11/14
356/3
5,617,209 A 4/1997 Svetkoff et al.
(Continued)

FOREIGN PATENT DOCUMENTS

DE 10260670 A1 7/2004
JP H1123485 A * 1/1999 ............. G01B 11/24
(Continued)

OTHER PUBLICATIONS

International Search Report for PCT/EP2011/070504 dated Mar. 12, 2012, 3 pages.
(Continued)

*Primary Examiner* — Melissa Koval
*Assistant Examiner* — Courtney McDonnough
(74) *Attorney, Agent, or Firm* — Reising Ethington P.C.

(57) ABSTRACT

A method and apparatus for testing the mounting of an integrated circuit on a printed circuit board using a ball grid array comprises directing an inclined laser beam from a line scan laser sensor at the integrated circuit, detecting the position of the lower edge of the integrated circuit from laser light backscattered from the integrated circuit and printed circuit board, determining through a trigonometric calculation the height of the integrated circuit above the printed circuit board following soldering of the ball grid array and comparing the height with reference data. The integrated circuit is deemed to have been successfully mounted to the printed circuit board if the height falls within a predetermined range.

20 Claims, 6 Drawing Sheets

(58) Field of Classification Search
USPC .......................................................... 324/501
See application file for complete search history.

(56) References Cited

U.S. PATENT DOCUMENTS

| | | | |
|---|---|---|---|
| 5,691,815 A | 11/1997 | Huber et al. | |
| 7,039,228 B1* | 5/2006 | Pattikonda | G01B 11/0608 348/87 |
| 7,840,371 B2* | 11/2010 | Gaspardo | G06T 7/0071 702/151 |
| 2008/0165357 A1* | 7/2008 | Stern | G01B 11/0608 356/364 |
| 2010/0183194 A1 | 7/2010 | Umemura et al. | |

FOREIGN PATENT DOCUMENTS

| | | |
|---|---|---|
| JP | H1123485 A | 1/1999 |
| WO | WO2006/011852 A1 | 2/2006 |
| WO | WO2010/108905 A1 | 9/2010 |

OTHER PUBLICATIONS

Written Opinion for PCT/EP2011/070504 dated Mar. 12, 2012, 6 pages.
UK Search Report for GB1119968.4, dated Dec. 23, 2011, 2 pages.
Co-Pending PCT Application No. PCT/EP2010/053747, filed on Mar. 23, 2010, 19 pages.
Heimann P A: Measurement of the Standoff Height Between a Flip-Mounted IC Chip and Its Substrate:, IEEE Transactions on Components, Hybrids, and Manufacturing Technology, IEEE Inc., New York, U.S., vol. 14, No. 1, Mar. 1, 1991, pp. 187-191, XP000227609, ISSN: -148-6411, DOI: 10.1109/33.76530 p. 3; figures 5, 6.

* cited by examiner

APPARATUS AND METHOD FOR INSPECTING PCB-MOUNTED INTEGRATED CIRCUITS

INTRODUCTION

The present disclosure relates to an apparatus and method for inspecting PCB-mounted integrated circuits and particularly, but not exclusively, integrated circuits mounted to a PCB or other substrate by means of a Ball Grid Array (BGA). Aspects of the invention relate to a method, to an apparatus, to an integrated circuit and to an electronic device.

BACKGROUND TO THE INVENTION

There are several techniques employed for surface-mounting integrated circuits (ICs) onto substrates such as printed circuit boards (PCBs). One common technique is the use of Ball Grid Arrays (BGAs) in which the pins of the IC are replaced by solder balls disposed on the underside of the IC package with the PCB carrying conductive pads in a pattern corresponding to the solder balls. In a technically-equivalent variation of this technique, the solder balls are formed instead on the PCB itself in a pattern that matches the pins of the IC.

Mounting the IC package to the PCB involves placing the IC in the correct position on the PCB substrate and then heating the assembly, for example by means of an oven or infrared heater, causing the solder balls to melt in a process called "reflow". During reflow, the IC is drawn down or sinks towards the substrate in two stages: a first drop caused by the surface tension of the melting solder and a second drop due to the subsequent contraction of the solder mass as it solidifies during cooling. Surface tension within the molten solder also tends to retain the package in the correct alignment on the substrate. The solder then cools and solidifies to form the desired electrical contacts.

IC packages using a similar solder-ball technology are known as "flip-chips", wherein the solder balls are deposited onto the top-side of the chip or wafer which is then flipped over and aligned with the matching pads on the PCB. The connections are again created by heating and melting the solder during the reflow process.

BGA packages have a number of advantages over conventional pin grid array (PGA) techniques, such as improved packaging and assembly and improved conductive and thermal performance. As a result, BGAs are becoming widely used globally, particularly for larger PCBs with many connections since they allow for higher density components.

On the other hand, as with many electronic systems, the soldering process is not wholly reliable and open contacts or short circuits maybe formed inadvertently. In particular, since the solder balls are substantially non-compliant (that is, unable to flex), thermal or mechanical stresses caused, for example, by differences in coefficients of thermal expansion between the PCB substrate and the BGA package or by flexing and vibration of the PCB, may cause the solder joints to fracture.

It is therefore conventional to perform some form of testing of the IC connections on the PCB after soldering. In order to maintain production efficiency, an automated inspection process is generally preferred. The automated inspection of electronic components is an integral part of electronic assembly manufacture to prevent and detect faults and to ensure quality and performance of the assembled systems. Increases in PCB complexity and the desire to improve yields have required the development of real-time automated inspection.

For example, visual inspection of a PCB can be performed using Automated Optical Inspection (AOI) in which a video camera is used to scan the assembly and compare the scanned image with pre-recorded images of properly soldered PCBs. Where conventional PGA soldering methods are used to mount the IC to the PCB, AOI can be used to determine the efficacy of the soldered joints. In the case of BGA-mounted ICs, however, AOI systems are usually unable to measure the integrity of the solder joints due to the position of the connections on the underside of the IC package and are therefore generally limited to diagnosing missing components and placement errors. This may lead to faults not being diagnosed using standard automated inspection techniques, resulting in faulty products and a loss of revenue for manufacturers.

Co-pending PCT Application No. PCT/EP2010/053747 in the name of the present applicants, the contents of which are expressly incorporated herein by reference, addresses this problem and discloses an automated inspection process in which a downwardly-directed laser measurement device positioned directly overhead the IC package detects the height of the package above the substrate before and after reflow. Specifically, the laser measurement device is positioned a predetermined height above the substrate and emits a beam substantially vertically downwards which is reflected from the top surface of the package onto an associated CCD camera, allowing the distance of the package from the device to be calculated. A second beam is then emitted and reflected from the surface of the substrate adjacent the package allowing the distance of the substrate from the device to be calculated.

Subtracting the first distance from the second gives the height of the top surface of the package from the substrate.

By calculating the height of the upper surface of the package above the substrate both before and after reflow, the drop of the package due to the reflow process can be calculated. The applicants have identified that a correctly soldered component will drop a predetermined amount during reflow. If one or more solder balls has not completely melted during soldering, then the component will remain supported without settling to the expected standoff height. If the measured drop is outside the predetermined range, the component is deemed to be mounted incorrectly. This method has been found to result in a high degree of accuracy in detecting improperly soldered packages.

It is against this background that the present invention has been conceived. While the applicants' prior technique produces more accurate results than previous methods, it is nevertheless an aim of the present invention to provide an improved technique for verification of the solder reflow process for soldered components, particularly BGA-soldered ICs, and to further increase accuracy. Embodiments of the invention may provide a method and/or apparatus that employs a conventional laser measuring device in a highly unconventional way to measure the height of a BGA-mounted IC or other package on a substrate.

The applicants have found that the claimed method and apparatus produces exceptionally and unexpectedly high accuracy, greatly surpassing the theoretical capabilities of the equipment employed. This enables the integrity of the soldered joints to be determined more quickly, more accurately and more cost-effectively in an automated process.

Other aims and advantages of the invention will become apparent from the following description, claims and drawings.

SUMMARY OF THE INVENTION

Aspects of the invention therefore provide an apparatus and a method as claimed in the appended claims.

According to another aspect of the invention for which protection is sought there is provided a method of inspecting the mounting of an electronic component on a substrate, comprising positioning a laser measurement device horizontally offset from the electronic component, tilting the laser measurement device through a predetermined angle relative to the vertical, operating the laser measurement device to direct an optical beam at the electronic component, at the predetermined angle, measuring the distance of each of a plurality of points on the electronic component from the laser measurement device by detection of backscattered light from said points and calculating the height of the electronic component above the substrate in dependence on the measured distances and the predetermined angle.

In an embodiment, the laser measurement device comprises a line-scan laser sensor or the like arranged to project a laser line onto the electronic component and/or the substrate.

In an embodiment, the method comprises projecting the line onto one or more of a portion of a side surface of the electronic component, a portion of the substrate adjacent to the electronic component, a portion of the substrate underneath the component and a portion of an upper surface of the electronic component.

In an embodiment the method comprises successively determining the position of each of a plurality of reflected points along the line corresponding to the position of each of the plurality of points on the electronic component.

In an embodiment the method comprises generating a line trace representative of the relative positions of each of the reflected points.

In an embodiment the method comprises integrating the plurality of measurements, for example using best fit lines, thereby to identify the relative positions of predetermined points on the electronic component and/or the substrate.

In an embodiment the step of measuring comprises measuring the distance of each of a first set of points on the electronic component, moving the laser measurement device relative to the electronic component, and measuring the distance of each of a second set of points on the electronic component adjacent to the first set of points.

In an embodiment the method comprises integrating the measurements for successive sets of points thereby to identify the relative positions of predetermined points on the electronic component and/or the substrate.

In an embodiment the predetermined points comprise at least a lower edge of the electronic component and a furthest point on the substrate under the component on which a laser line projected by the laser measurement device is incident.

In an embodiment the step of tilting comprises tilting or rotating the laser measurement device about an axis transverse to the direction of the beam.

In an embodiment the step of tilting comprises tilting or rotating the laser measurement device about an axis transverse to a line projected onto the substrate and/or electronic component by the beam.

In an embodiment the predetermined angle is between 10° and 80° from vertical, preferably between 30° and 60° from vertical, more preferably between 40° and 60° from vertical.

In an embodiment the predetermined angle is approximately or substantially 45° from vertical.

In an embodiment the step of operating the laser measurement device comprises projecting a laser line onto the substrate and the electronic component and wherein the step of calculating comprises determining the length of the laser line incident on a portion of the substrate disposed beneath the electronic component and calculating the height h of the component above the substrate using the equation $h = L \cos\theta$ wherein L is the length of the shadow under the component and $\theta$ is the predetermined angle.

In an embodiment the method comprises comparing the height of the component above the substrate with a reference height and determining whether the component is correctly mounted on the substrate in dependence on the comparison.

In an embodiment the reference height comprises a height of the component above the substrate prior to a soldering process for electrically connecting the component to the substrate.

In an embodiment comparing the height of the component relative to the reference height comprises measuring a first height of the component above the substrate, performing a soldering process to electrically connect the component to the substrate, measuring a second height of the component above the substrate after the soldering process and comparing the first and second heights.

In an embodiment the method comprises determining that the component is correctly mounted on the substrate if the difference between the height of the component before the soldering process and the height of the component after the soldering process falls within a predetermined range and/or determining that the component is not correctly mounted on the substrate if the difference between the height of the component before the soldering step and the height of the component after the soldering step falls outside a predetermined range.

In an embodiment the predetermined range is between approximately 50 μm and 750 μm, the precise values being dependent on the size of the solder ball used. For example, for a 300 μm diameter solder ball the predetermined range is between approximately 160 μm and 200 μm.

In an embodiment the method comprises determining that the component is not correctly mounted on the substrate if the height of the component after the soldering step is not substantially the same for each of the predetermined points in each set of points.

In an embodiment the substrate comprises a printed circuit board and the component comprises an integrated circuit or IC package for mounting to the PCB by means of a plurality of solder balls.

According to another aspect of the invention for which protection is sought there is provided an apparatus adapted or arranged to perform a method as set out in any one or more of the preceding paragraphs in this Summary.

According to yet another aspect of the invention for which protection is sought there is provided an apparatus for inspecting the mounting of an electronic component on a substrate, the apparatus comprising a line scan laser measurement sensor, positioning means for moving the sensor to a position laterally or horizontally offset from the electronic component, tilt means for tilting and/or rotating the sensor relative to the electronic component about an axis transverse to an optical beam emitted by the sensor and/or to a line projected onto the electronic component and/or the substrate by the beam and processor means for calculating the height of the electronic component above the substrate in dependence on the relative positions of points on the electronic component and/or the substrate measured by the sensor and an angle of tilt of the sensor.

In an embodiment the positioning means comprises a X-Y Cartesian robot or the like.

In an embodiment the tilt means comprises arcuate guide means arranged to tilt the sensor to a predetermined angle relative to the vertical. In an embodiment the positioning means comprises the arcuate guide means.

In an embodiment the apparatus further comprises rotation means for rotating the sensor relative to the electronic component about a substantially vertical axis.

In an embodiment the rotation means is arranged to rotate the arcuate guide means relative to the electronic component about a substantially vertical axis.

According to a further aspect of the invention for which protection is sought, there is provided a method for inspecting the mounting of an integrated circuit on a printed circuit board using a ball grid array comprising directing an inclined laser beam from a line scan laser sensor at the integrated circuit, detecting the position of the lower edge of the integrated circuit from laser light backscattered from the integrated circuit and/or the printed circuit board, determining through a trigonometric calculation the height of the integrated circuit above the printed circuit board following soldering and comparing the height with reference data.

In an embodiment, the integrated circuit is deemed to have been successfully mounted to the printed circuit board if the height falls within a predetermined range.

Within the scope of this application it is envisaged that each of the various aspects, embodiments, examples, features and alternatives set out in the preceding paragraphs, in the claims and/or in the following description and drawings may be taken independently or in any combination thereof. For example, features described in connection with one embodiment are applicable to other embodiments, unless there is an incompatibility of features.

DETAILED DESCRIPTION OF EMBODIMENTS OF THE INVENTION

The present invention will now be described, by way of example only, with reference to the accompanying drawings in which.

Figure 1A:
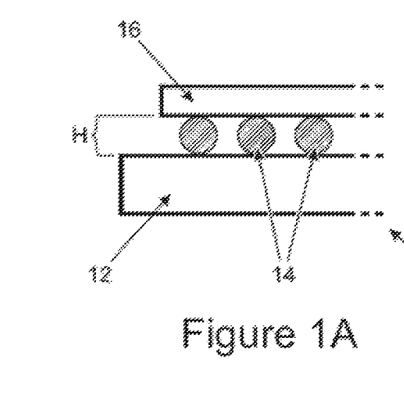
FIGS. 1A and 1B illustrate schematically sections through a solder joint between an IC and a PCB before and after soldering, respectively.

Referring to FIG. 1A, which is schematic and not shown to scale, a portion of a BGA assembly prior to soldering is shown in cross section generally at 10. The BGA assembly 10 may comprise a part of an electronic circuit for incorporation within an electrical device. The BGA assembly 10 comprises substrate in the form of a PCB 12 having three solder balls 14 formed on its upper surface. An electronic component, in the form of an IC package 16, to be mounted on, and electrically connected to, the PCB 12, is seated on the solder balls 14. It can be seen that, prior to soldering, the solder balls 14 are generally uniform in shape such that the IC package 16 is spaced from the PCB 12 by a first distance H.

In the illustrated embodiment, the solder balls 14, constituting part of the BGA, are formed on the upper surface of the PCB 12 and the IC package 16 is positioned such that the solder balls 14 are coincident with corresponding conductive pads on the underside thereof. In other embodiments (not shown), the solder balls 14 may instead be formed on the underside of the IC package 16 which is placed onto the PCB 12 such that the solder balls 14 are coincident with corresponding solder pads formed on the upper surface thereof.

It will be appreciated that, in practice, the BGA 10 may comprise many, perhaps even hundreds, of solder balls 14, depending on the application. For clarity, however, only three solder balls 14 are shown and described here.

Figure 1B:
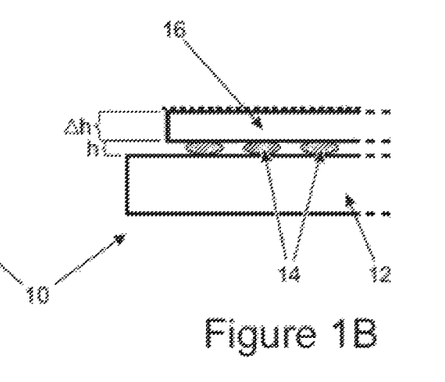

During soldering, the assembly is heated such that the solder balls 14 melt in a process called reflow so as to electrically connect the IC package 16 to the PCB 12. Reflow of the solder balls 14 causes them to deform, spreading out over the corresponding contact regions (conductive pads) of the IC package 16. As shown in FIG. 1B and described above, melting of the solder balls 14 causes the IC package 16 to be drawn down towards the upper surface of the PCB 12 such that, after soldering, the IC package 16 is spaced from the PCB 12 by a second, reduced distance h.

As with any soldering process, there is the possibility of poor or faulty connections being formed between the IC package 16 and the PCB 12. Since a single faulty contact, for example an open or a short, can affect the function of the entire electronic circuit, it is conventional to test or inspect the mounting of the IC package 16 on the PCB after soldering. The demands of production efficiency require such testing to be automated and both fast and reliable.

Figure 2:
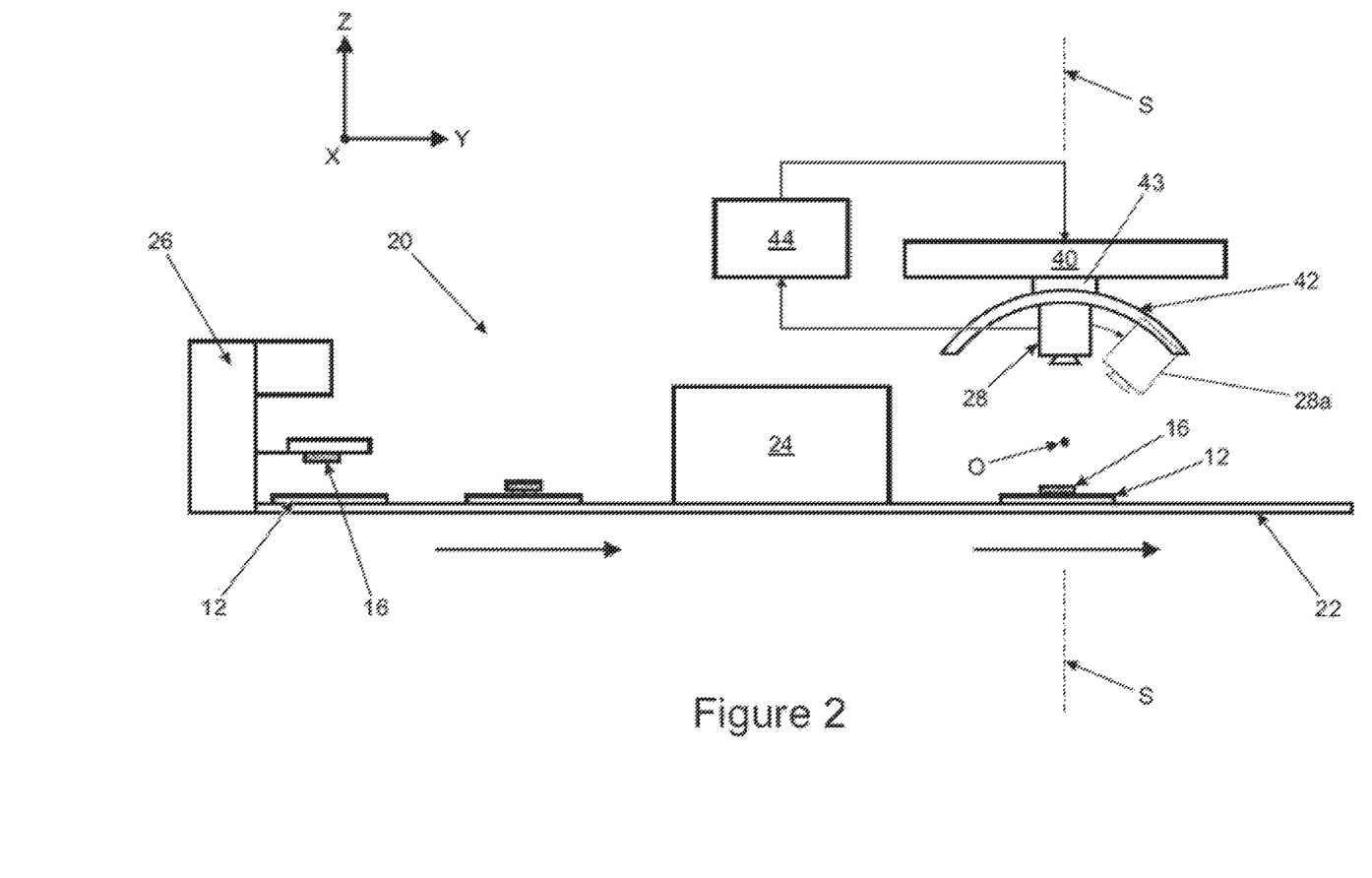
FIG. 2 illustrates schematically an apparatus embodying one form of the invention.

Referring next to FIG. 2, an apparatus embodying one form of the invention is shown, in schematic form, generally at 20. The apparatus comprises transport means, in the form of a conveyor system or similar transport device 22, arranged to convey BGA assemblies, consisting of PCBs 12 carrying one or more ICs 16 thereon, through a reflow soldering unit 24.

Figure 3:
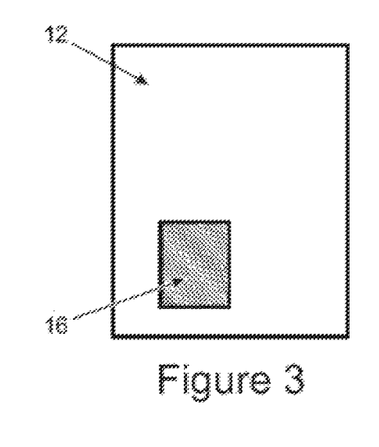
FIG. 3 is a plan schematic view of a PCB having an IC mounted thereon by means of a ball grid array.

The apparatus 20 comprises a placement unit 26 arranged to place each IC package 16 in its correct position on the PCB 12 for mounting thereto. FIG. 3 illustrates, schematically and in plan view, a PCB 12 having an IC package 16 placed on it by means of the placement unit 16. As described above, the PCB 12 carries a solder ball array (BGA) comprising a plurality of solder balls 14 for electrically connecting the PCB 12 to the corresponding conductive pads on the underside of the IC package 16. The placement unit 26 is therefore required to position the IC package 16 on the solder ball array which cannot be seen in FIG. 3 since it lies beneath the IC package 16 itself.

Mounting the IC package 16 to the PCB 12 involves melting the solder balls 14 in the array to form the desired electrical connections therebetween and is achieved by means of the reflow soldering unit 24. The reflow soldering unit 24 may comprise a reflow oven or infrared heater arranged to apply thermal energy to the BGA assembly so as to cause melting, or reflow, of the solder balls 14.

In use, therefore, the PCB 12, with the IC package 16 having been placed thereon by the placement unit 26, is transported through the reflow soldering unit 24 by the transport device 22. On leaving the reflow soldering unit 24, the PCB 12 with the IC package 16 soldered thereto is transported to other parts of the manufacturing process for further assembly. This form of manufacturing apparatus will be well understood by the skilled person and further detail is not provided herein.

In order to test the mounting of the IC package 16 to the PCB 12, for example to check the reliability and integrity of the solder joints between the IC package 16 and the PCB 12, the apparatus 20 comprises measurement means in the form of at least one laser measurement device 28 for measuring or detecting the position of the IC package 16 relative to the PCB 12. In the illustrated embodiment, a single laser measurement device 28 is disposed above the conveyor 22 downstream of the reflow soldering unit 24 for measuring the position of the IC package 16 after reflow. In other, optional, embodiments, an additional laser measurement device is provided upstream of the reflow soldering unit 24 for measuring the position of the IC package 16 before reflow. The laser measurement device 28 is connected to control means, in the form of a processor 44, for controlling and monitoring the position of the laser measurement device 28 and for receiving and processing measurement signals generated thereby.

Figure 4:
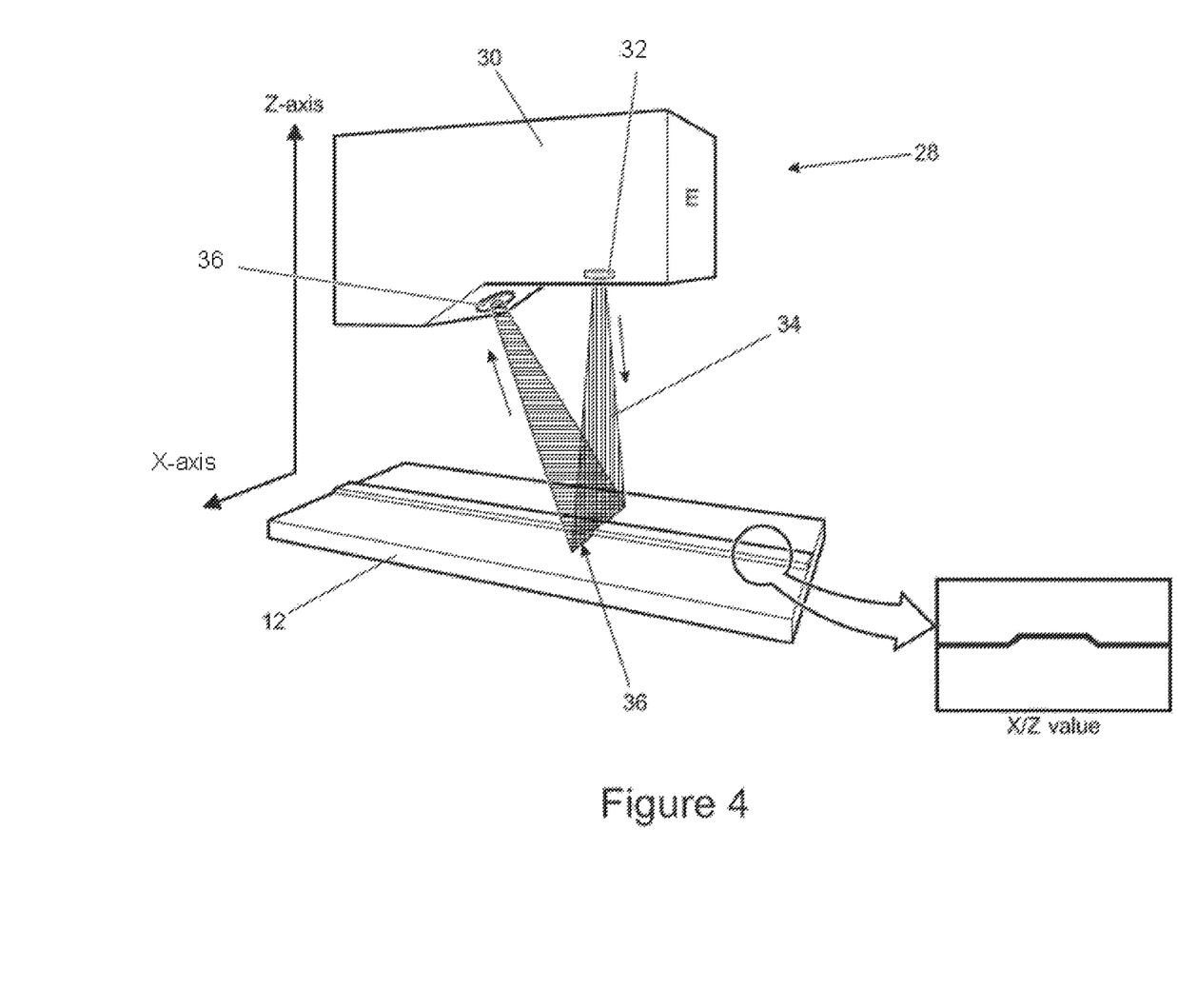
FIG. 4 illustrates an example of a laser measurement device forming part of the apparatus of FIG. 2.

In the non-limiting illustrated embodiment, the laser measurement device 28 advantageously comprises a laser triangulation sensor 28 arranged to measure the position of a target object by means of triangulation. An example of one such sensor is a line-scan sensor device manufactured and sold by Micro-Epsilon under the product name "OptoNCDT sensor". This type of sensor, illustrated in more detail in FIG. 4, generally comprises a housing 30 containing a laser diode 32 arranged to emit a highly directional, fan-shaped optical beam 34 which is projected onto the surface of a target object (e.g. IC package 16) in the form of a line 36 having a length substantially greater than its width. For example, the width of the line 36 may be in the order of a few microns (μm), while the length of the line may be several centimetres in length, as shown in FIG. 4.

An optical lens system focuses backscattered laser light from the target object 16 onto an optical sensor 38, such as CCD camera or device, contained within the housing 30 with the light appearing at different places in the sensor's field of view depending on the distance of the target object 16 from the device 28. A processor (not shown) within the laser measurement device 28 determines, using triangulation, the position and/or movement of the target object 16 relative to the sensor in a manner which is well known and would be fully understood by the skilled artisan, further explanation being considered unnecessary.

In the apparatus of FIG. 2, the laser measurement device 28 is movable relative to the conveyor 22, and hence relative to the IC package 16 mounted thereon. Specifically, the laser measurement device 28 is supported from a conventional X-Y stage transport device 40, such as a Cartesian robot, arranged to move the device 28 generally horizontally in both X- and Y-directions relative to the conveyor 22, that is to say both parallel to the conveyor direction and transverse thereto. Such X-Y transport devices 40 are well known in the art and further description is considered unnecessary. Cartesian axes are shown in FIG. 2 to aid understanding.

In addition, the laser measurement device 28 is arranged to rotate or tilt about a generally horizontal axis extending transversely to the beam 34 and to the projected line 36. In the illustrated embodiment, the laser measurement device 28 is mounted to guide means in the form of a pair of parallel, arcuate guide rails 42. Drive means (not shown) is arranged to move the laser measurement device 28 along the rails 42 causing it to rotate about the axis O defined by the geometric centre of the circle proscribed by the arcuate guide rails 42. In the illustrated embodiment, the curve of the rails 42 subtends an angle of approximately 150°, although substantially any desired angle can be selected depending on the application.

When positioned at the midpoint of the rails 42, the laser measurement device 28 is directed substantially vertically downwardly and the fan-shaped laser beam is projected onto the target object as a substantially horizontal line. This position is shown in FIG. 2 by the solid-line image of device 28.

Movement of the laser measurement device 28 along the guide rails 42 away from the midpoint, however, causes the device 28 to rotate or tilt about the axis O such that the fan-shaped laser beam 34 is projected towards the target object at an angle θ to the vertical determined by the angular displacement of the device 28 along the rails 42. In this position of the laser measurement device, represented by the dotted-line image of device 28*a* in FIG. 2, the projected laser line 36 has both horizontal and vertical components and thus illuminates or "paints" both horizontal and vertical surfaces of the target object within line of sight of the device 28.

The laser measurement device 28 is also arranged for rotation about a substantially vertical axis S relative to the conveyor 22. In one embodiment, this is achieved, for example, by mounting the guide rails 42 to the X-Y stage transport device 40 by a rotatable mount 43 which is driven by means of a stepper motor or the like (not shown).

Alternatively, the laser measurement device 28 may be mounted to the X-Y stage transport device 40 by a tilt-swivel mount allowing it to be tilted or rotated about a longitudinal axis A extending transverse to the projected laser line 36 and rotated about the vertical axis S. In other embodiments (not shown), the X-Y stage transport device 40 it is itself rotatable relative to the target object 16.

It will be understood from the foregoing that various arrangements may be adopted to mount the laser measurement device 28. In each arrangement, however, the laser measurement device 28 is able to translate in X- and Y-directions relative to the conveyor 22 (and hence relative to the IC package 16) and also to rotate about a vertical axis S and to tilt about a substantially horizontal axis O transverse to the projected laser line 36. It will be further appreciated that the relative positioning and orientation of the laser measurement device 28 with respect to the target object may be achieved, either partially or in full, by corresponding movement or orientation of the target object itself in addition to, or instead of, movement of the laser measurement device 28. For example, the IC package 16 may be supported on a rotatable table on the conveyor 22 for rotation about a vertical axis S relative to the laser measurement device 28.

Control means, in the form of an electronic controller or processor 44, is connected to the X-Y stage transport device 40 and to the laser measurement device 28 for controlling the above-described lateral, tilting and rotational movement of the laser measurement device 28 and for receiving and processing signals from the laser measurement device 28.

During inspection of the soldered IC package 16 following reflow, the X-Y stage transport device 40 is controlled by the processor 44 to move the laser measurement device 28 so that it is laterally (horizontally) offset from the target object (IC package 16). The laser measurement device 28 is then tilted relative to the IC package 16, for example by movement along the guide rails 42, so that the laser beam 34 is projected towards the IC package 16 at a predetermined angle of inclination θ relative to the vertical.

The applicants have discovered that laterally (horizontally) offsetting the laser measurement device 28 from the IC package 16 and directing the laser beam 34 at the IC package 16 at an inclined angle θ to the vertical enables the height h of the lower edge or underside of the IC package 16 above the substrate 12 to be directly measured in a single scan. The skilled person will readily appreciate that laser measurement devices 28 of the type described are intended to be used in a vertical orientation projecting a laser beam 36 substantially vertically downwards from a position directly overhead the target object, as shown in FIG. 4.

The horizontally offset and tilted position of the laser measurement device 28 employed in the present implementation therefore goes wholly against conventional methods of operation of such devices. It is noted, in fact, that when approached by the applicants during development of the present invention, manufacturers of laser measurement devices of the type described above advised that the devices could not be used in such an orientation, for example due to backscattering losses caused by the increased angle of incidence onto the target object. On the contrary, however, the applicants discovered that not only was measurement of the height of the IC package 16 possible, but the degree of accuracy of measurement was many times greater than expected.

Figure 5:
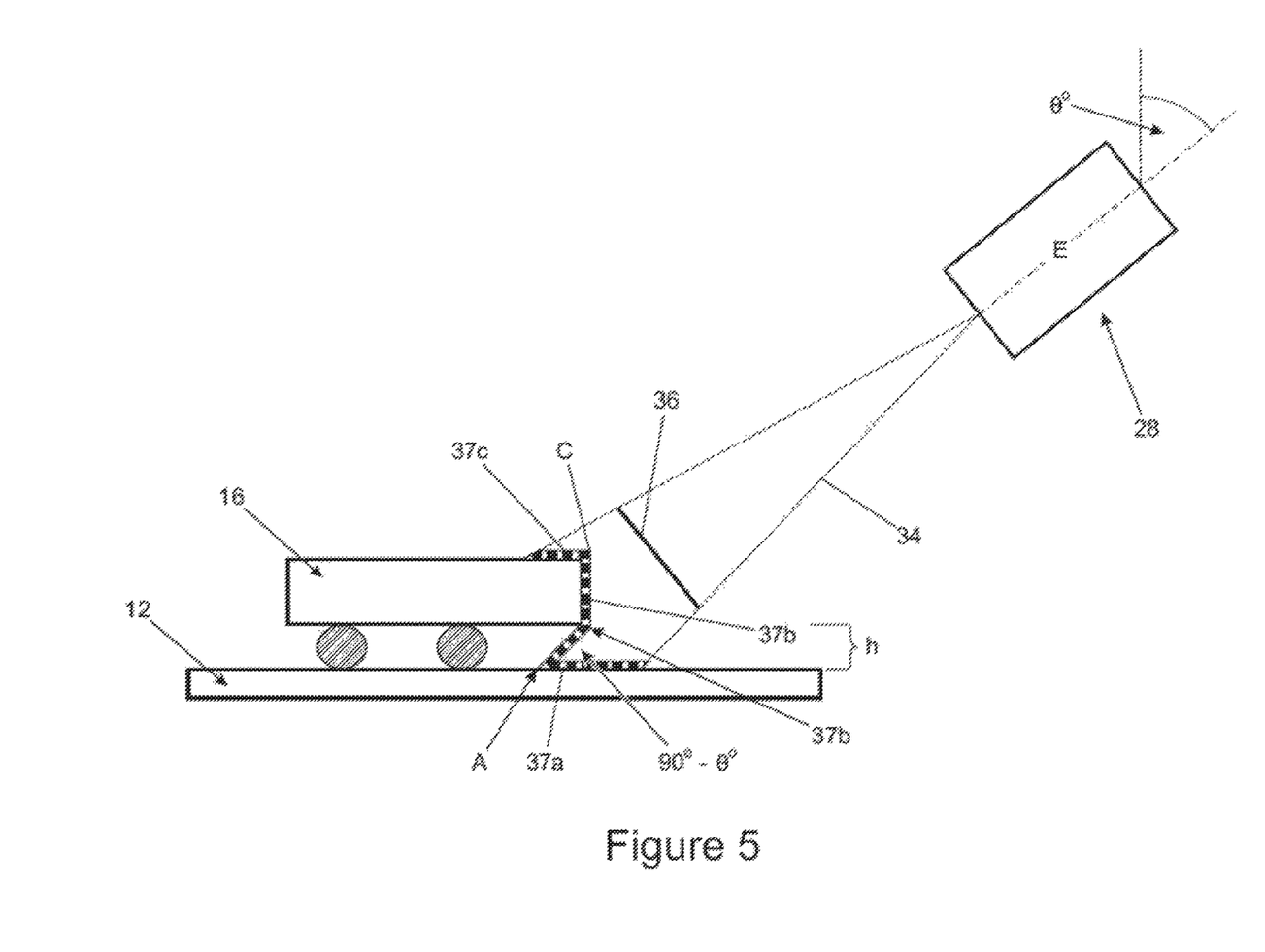
FIG. 5 illustrates operation of the laser measurement device of FIG. 4 in the apparatus of FIG. 2.

FIG. 5 illustrates the laser beam 34 illuminating the target object (IC package 16). As shown in the Figure and described above, the laser measurement device 28 is both vertically and horizontally offset from the IC package 16 and is rotated or tilted through a known angle θ relative to the vertical (for example approximately 45°) having been moved along the guide rails 42 relative to the IC package 16. In this position, the projected laser line 36 has both horizontal and vertical components and thus illuminates or "paints" both horizontal and vertical surfaces of the IC package 16.

For clarity, in FIGS. 2, 4 and 5 a common end face of the laser measurement device 28 is represented by the letter E so that the direction and orientation of tilt of the device 28 can be more easily understood.

The diagonal line 36 represents the notional wavefront of the laser beam 34 emitted by the laser measurement device 28. The wavefront is a substantially one-dimensional line 36 having a length significantly greater than its width and a small projected footprint, for example less than 100 um$^2$. Dotted line 37 illustrates the laser line 36 as it impinges upon the IC package 16. As illustrated, the laser line 36 illuminates a portion of the substrate 12 adjacent to the IC package 16 and extends partially under the IC package 16 by an amount dependent upon the angle θ and the height of the IC above the substrate 12 (dotted line 37a). The laser line 36 also illuminates the vertical side surface of the IC package 16 facing the laser measurement device 28 (dotted line 37b) and the upper surface of the IC package 16 (dotted line 37c).

As will be understood by the skilled artisan, the laser line 36 consists of a plurality of discrete points incident on the surface of the IC package 16, the distance of each of which from the laser measurement device 28 is calculated sequentially by the sensor and/or processor by means of a simple trigonometric calculation using the known inclination angle θ of the laser beam 34. For example, from the known angle θ of the laser beam 34 relative to the vertical and the length of the shadow from the edge of the IC package 16 (represented by line A-B), the height h of the IC package 16 can be calculated.

Figure 6:
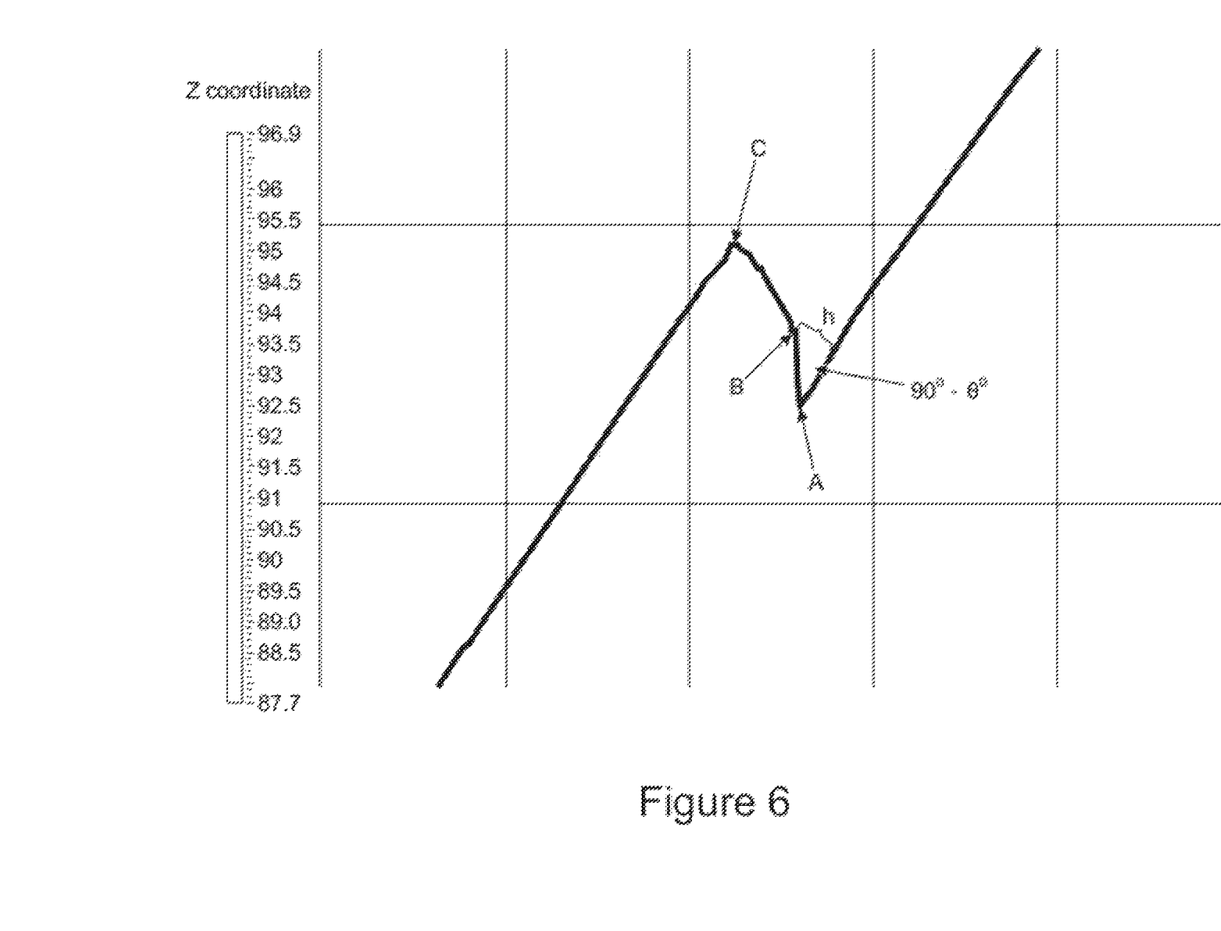
FIG. 6 shows an example of a first output trace from the laser measurement device.

The laser measurement device 28 scans along the laser line 36 (i.e. the dotted line 37) measuring the distance of each of the discrete points and generates an output trace, such as that shown in FIG. 6, representative of the relative positions of each point, and thus the corresponding position of the surface of the IC package 16.

It can be seen from FIG. 6 that the single line output trace matches substantially exactly the shape of the laser line 36 (dotted line 37) impinging upon the IC package 16. Specifically, if the dotted line 37 in FIG. 5 is rotated anticlockwise through approximately 45 degrees, it substantially precisely overlays the output trace line shown in FIG. 6.

The applicants have also found that the relatively low resolution sample points along the laser line 36 as it goes into the shadow can be optimised through integration of the best fit lines for the vertical edge of the IC package 16 and the line length into the shadow of the IC package 16 (line A-B) so that the intersection of these lines represents the desired measurement points for calculating the height h.

The trace line of FIG. 6 thus clearly shows the step changes in the positional measurements when the laser line 36 impinges upon the vertical side face of the IC package 16. In particular, the points A, B and C illustrated in FIG. 5 are clearly represented in the trace line of FIG. 6.

Although not specifically shown in FIG. 5 due to lack of space, it will be recognised that the angle between the line A-B (termed hereafter the shadow line) and the vertical (i.e. a line normal to surface of the substrate 12) is equal to the predetermined tilt angle θ. Instead, in FIG. 5 only the angle between the line A-B and the horizontal surface of the substrate 12 is shown as (90°-θ°), thereby implicitly showing the angle θ.

The height h of the IC package 16 above the substrate 12 can therefore be calculated from the length L of the shadow line A-B and the inclination angle θ using the formula:

$$h = (A-B) \cosine \theta \qquad (1)$$

From this calculation, it can be determined whether the height h of the IC package 16 above the substrate 12 falls within the range that would be expected of a correctly soldered component. For example the post-soldered height h may be compared with reference data relating to the height H of the component above the substrate prior to solder reflow and the drop in height due to reflow calculated therefrom. The processor 44 then checks to determine whether the calculated drop amount (Δh) falls within a predetermined range indicative of a good solder connection in order to provide a Pass/Fail result.

For example, if the IC package 16 is determined to have dropped by an amount within the predetermined range, the mounting of the IC package 16 to the PCB 12 is deemed to have been successful and the processor outputs a Pass result. On the other hand, if the IC package 16 has dropped by an amount which falls outside the predetermined range, the mounting of the IC package 16 to the PCB 12 is deemed to have been unsuccessful and the processor 44 outputs a Fail result. In this case, the PCB 12 may be returned into the solder reflow unit 24 for resoldering, removed for further processing or testing, or rejected.

At least certain implementations of the present invention rely on the discovery that once the BGA assembly is heated in the reflow process the IC package 16 is drawn towards the surface of the PCB 12. As described above, the applicants have recognized that an IC package 16 will drop a substantially fixed distance when all the joints are successfully made and that, for good quality connections to be achieved, each joint should drop by approximately the same amount.

The applicants have further determined that the optimum drop distances range between 50 μm and 750 μm, the precise values being dependent on the size of the solder ball used hereafter termed Range A. For example, for a 300 μm diameter solder ball the Range A is between approximately 160 μm and 200 μm. If this consistent drop within Range A is not achieved during the reflow process, it suggests that the soldered connections are not of an acceptable quality. In one embodiment, therefore, the following criteria may be used to evaluate the results of the measurement process:

a) If the height drop ($\Delta h$) of the IC relative to the PCB is less than Range A, then this indicates the presence of one or more open contacts;

b) If the height drop ($\Delta h$) of the IC relative to the PCB is more than Range A, then this indicates the presence of short circuits;

c) If height drop ($\Delta h$) is not consistent across the IC package 16, then the package is tilted or inclined relative to the PCB 12 which may be indicative of a combination of one or more open contacts and one or more shorts.

Figure 7:
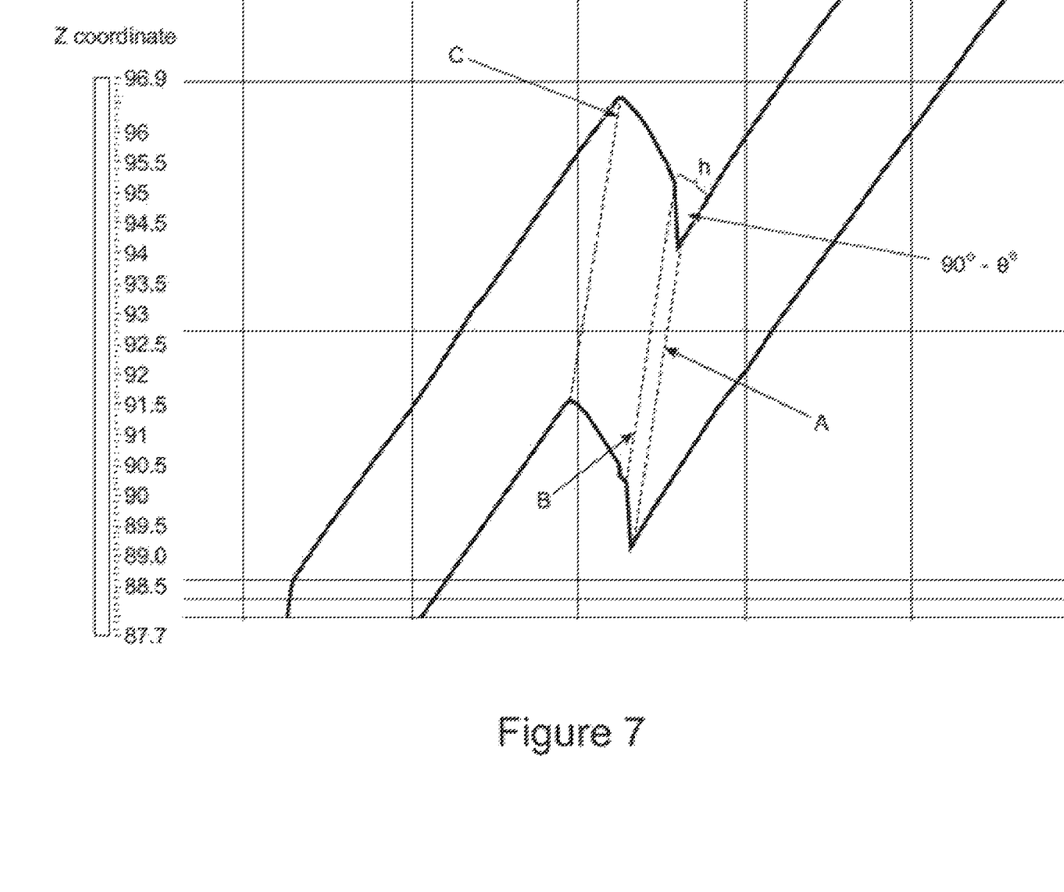
FIG. 7 illustrates an example of a second output trace from the laser measurement device.

In one embodiment, the laser measurement device 28 is linearly scanned along the edge of the IC package 16, by translational movement of the device in the appropriate X- or Y-direction(s) by means of the X-Y stage transport device 40, taking single line scan measurements approximately 80 μm apart. This process results in a stacked sequence of line traces as shown in FIG. 7, each line trace representing a single line scan spaced from adjacent scans by approximately 80 μm. Other sample distances are possible, however, and the applicants have obtained advantageous results using line scans from as little as 10 μm apart (significantly less than the beam width, meaning that adjacent scans overlap considerably) to as high as 100 μm apart or greater. FIG. 7 also shows, by dotted lines, the positions of points A, B and C in the stacked sequence.

While the resolution of the linear scan is relatively high, the applicants have realised that a high degree of randomisation/noise is present in the output data due to specular reflection from the surfaces of the IC package 16 and have discovered that integrating the stacked line traces yields an unexpectedly significant improvement in accuracy resolution. The high density of well correlated but noisy signals from successive laser lines has been found to be highly suitable for integration techniques.

For example, the applicants have determined that such integration can enable the apparatus to measure the height of the IC package 16 above the PCB 12 to approximately 2-6 μm, almost an order of magnitude more highly resolved than the theoretical optimum performance of the laser measurement device 28.

By effecting appropriate movement of the X-Y stage transport device 40, and appropriate tilting and rotation of the laser measurement device 28 relative to the target IC package 16, the laser measurement device 28 can be controlled to scan along some or all side faces of the IC package 16 in order to determine the height above the substrate of the entire perimeter of the package. For each face, the laser measurement device 28 is offset horizontally and vertically from the target IC package 16 and tilted by a known angle θ to project an inclined beam 34 towards the edge under test.

The laser measurement device 28 is then linearly scanned over the PCB substrate 12 adjacent to and normal to the edge of the IC package 16, recording the distance from the sensor to the target surface of the IC package 16 by taking multiple single line scans as described above. Each single line scan is integrated to determine the appropriate measurement points, being the lower edge of the respective side face under test (point B in FIG. 5) and the furthest point on the substrate 12 under the IC package 16 on which the laser line 36 is incident (point A in FIG. 5), and the height h of the lower edge above the substrate 12 for that scan position is then calculated using equation (1) above. The sequence of stacked line traces are then integrated to obtain the overall height measurement which, as described above, exhibits an exceptional and unexpectedly high accuracy.

The angled beam 34 extends under the IC package 16 sufficiently to easily detect and measure the step change when the lower edge of the component is detected (i.e. the height of the solder joint). Similarly the continuing linear scan of the sensor detects the top edge of the component. The angled height profile also shows the component edge thickness in the same height profile as scanned across the PCB immediately adjacent to the component and normal to the component edge to continue the height profile scan over at least the top edge of the soldered component. The component thickness can be compared to manufacturers data as quality check on the lower edge height above the PCB measurement.

The present invention improves significantly on known systems and measurement methods. In addition to significantly improved accuracy, the method may require only a single measurement for each point on the IC package 16. This is in contrast to co-pending application no. PCT/EP2010/053747 in which separate and successive measurements of the position of the upper surface of the IC package 16 and the position of the PCB 12 adjacent thereto are required to determine the height h of the IC package 16.

In the illustrated embodiment, a single post-reflow scan is made of the IC package 16. Such a technique requires the measured height of the IC package 16 to be compared with reference data, such as component dimensions or pre-reflow production line examples. Modern mass produced components are very consistent within a batch in their dimensions, particularly the thickness of cavity packed semiconductor integrated circuits. The measurement process accurately determines the PCB to underside of component height h and the component thickness such that subsequent measurements of the top surface of the component above the PCB substrate can then be used to indirectly measure the solder height.

In another embodiment, however, an additional laser measurement device is provided upstream of the reflow soldering unit 24 for measuring the height of the IC package 16 above the substrate 12 prior to reflow with the conveyor 22 transporting the product under each X-Y stage transport device 40. The pre- and post-reflow height measurements can then be compared in order to calculate the reflow drop Δh independently of component batch manufacturing tolerances.

The use of an X-Y stage transport device 40 permits multiple IC packages 16 to be inspected sequentially and rapidly while the PCB 12 is on the conveyor 22. It will be appreciated, however, that where the arcuate guide rails 42 are provided to effect the required tilting of the laser measurement device 28, movement of the device 28 along the rails may itself cause the device 28 to become sufficiently laterally (horizontally) offset from the target IC package 16 to enable the inclined beam 36 to impinge upon a portion of the substrate 12 under the package 16. The use of the X-Y stage transport device 40 is therefore to be considered advantageous, but non-essential.

Immediate feed back of statistical fault locations enable the production line process to be modified for solder paste, PCB and component cleanliness, reflow oven profile etc to be adjusted and rework to be undertaken before expensive testing is undertaken.

The specific measurement points combined with the tight resolution (+/−2 um) relative standoff (component height) as measured around the edge and corners of a component such as a grid array solder ball enable the system to easily keep up with production line assembly rates allowing 100% real-time inspection of the selected components on every PCB assembly.

The system can accommodate the limited standoff change (<50 um) of non-eutectic solder balls as used on ceramic and copper framed BGAs where the solder balls do not melt but the eutectic solder paste applied to the PCB pads does melt.

The angled height measurement enables the lower edge (i.e. the underside edge nearest the PCB surface 12) of the soldered component 16 to be measured directly from the scanned profile line without inference or differential intermediate method or reliance on component manufacturers data.

Repeating the top surface height above adjacent PCB substrate measurement at the corners of the component and if possible along the edges enables the detection of incompletely melted solder as an indicator of incomplete reflow process. The component can then be shown to be coplanar with the PCB substrate as desired or settled at an angle possibly due to incomplete solder reflow (balls/columns not melted completely) or subject to warpage (component or substrate).

Height profiling of significant parts or the whole of the PCB substrate can resolve warpage as this may threaten the coplanarity of component attachment or stress in the assembly when mounted in the final product assembly.

Vertical distance sensors may be used to scan the relative height of parts or the whole of the PCB. The height information contains the profile of uncovered (end of chip, J-lead etc) solder joints which can be automatically determined to confirm solder meniscus to be compliant with IPC requirements.

A single height of lower edge above PCB measurement h is sufficient to calibrate any other top surface height of component above the PCB measurements for each specific component type.

While embodiments of the present invention have been described with reference to a conventional ball grid array, the invention is equally applicable to more advanced integrated circuit packaging techniques such as Package-on-Package (POP) technology in which two or more IC packages are vertically stacked and connected via ball grid arrays.

POP technology improves packaging density but is extremely difficult to inspect using even AXI techniques which are generally unable to distinguish between the stacked BGAs and therefore incapable of identifying soldering faults with acceptable accuracy. The present invention, on the other hand, advantageously permits identification of soldering faults even in POP PCBs with multiple-stacked BGAs.

This application claims priority from UK patent application no. GB1019537.8 filed 18 Nov. 2010, the entire contents of which are expressly incorporated herein by reference.

The invention claimed is:

1. A method of determining the spacing between a substrate and an electronic component mounted thereon, the method comprising:

positioning a line scan laser measurement device laterally or horizontally offset from the electronic component;

tilting the line scan laser measurement device through a predetermined angle relative to the vertical;

operating the line scan laser measurement device to project a laser line onto the substrate and the electronic component, the laser line being inclined at the predetermined angle relative to the substrate such that it extends at least partially under the electronic component;

measuring a first distance from the line scan laser measurement device to at least one first point on a portion of a surface of the electronic component by detection of backscattered light from said first point;

measuring a second distance from the line scan laser measurement device to at least one second point on a portion of the substrate underneath the electronic component by detection of backscattered light from said second point; and calculating the height of the electronic component above the substrate in dependence on the difference between the first and second measured distances and the predetermined angle.

2. A method as claimed in claim 1 wherein the line scan laser measurement device comprises a line-scan laser sensor.

3. A method as claimed in claim 2 comprising projecting the line onto one or more of:

a portion of a side surface of the electronic component;

a portion of the substrate adjacent to the electronic component; or a portion of an upper surface of the component.

4. A method as claimed in claim 2, comprising successively determining the position of each of a plurality of reflected points along the line corresponding to the position of each of the points on the electronic component and the substrate.

5. A method as claimed in claim 4 comprising generating a line trace representative of the relative positions of each of the reflected points.

6. A method as claimed in claim 4 comprising integrating the plurality of measurements thereby to identify the relative positions of predetermined points on the electronic component and/or the substrate.

7. A method as claimed in claim 1, wherein the step of measuring comprises:

measuring the distance of each of a first set of points on the electronic component;

moving the line scan laser measurement device relative to the electronic component; and measuring the distance of each of a second set of points on the electronic component adjacent to the first set of points.

8. A method as claimed in claim 7, comprising integrating the measurements for successive sets of points thereby to identify the relative positions of predetermined points on the electronic component and/or the substrate.

9. A method as claimed in claim 8, wherein the predetermined points comprise at least a lower edge of the electronic component and a furthest point on the substrate under the component on which a laser line projected by the line scan laser measurement device is incident.

10. A method as claimed in claim 1, wherein the step of tilting comprises tilting or rotating the line scan laser measurement device:

about an axis transverse to the direction of the beam; and/or about an axis transverse to a line projected onto the substrate and/or electronic component by the beam.

11. A method as claimed in claim 1 wherein the predetermined angle is between 30° and 60° from vertical.

12. A method as claimed in claim 1 wherein the step of calculating comprises determining the length (L) of a shadow of the laser line incident on a portion of the substrate beneath the electronic component and calculating the height (h) of the component above the substrate using the equation:

h=L cosine θ, where θ is the predetermined angle.

13. A method as claimed in claim 1 comprising comparing the height h of the component above the substrate with a reference height and determining whether the component is correctly mounted on the substrate in dependence on the comparison;
wherein the reference height comprises a height of the component above the substrate prior to a soldering process for electrically connecting the component to the substrate;
wherein comparing the height of the component relative to the reference height comprises:
measuring a first height of the component above the substrate;
performing a soldering process to electrically connect the component to the substrate;
measuring a second height of the component above the substrate after the soldering process; and
comparing the first and second heights;
wherein the step of determining whether the component is correctly mounted comprises determining that the component is correctly mounted on the substrate if the difference between the height of the component before the soldering process and the height of the component after the soldering process falls within a predetermined range; and/or
wherein the step of determining whether the component is correctly mounted comprises determining that the component is not correctly mounted on the substrate if the difference between the height of the component before the soldering step and the height of the component after the soldering step falls outside a predetermined range between approximately 50 μm and 750 μm.

14. A method as claimed in claim 7 comprising determining that the component is not correctly mounted on the substrate if the height of the component after the soldering step is not substantially the same for each of the predetermined points in each set of points.

15. A method as claimed in claim 7, wherein the second set of points is spaced from the first set of points by a distance of between approximately 10 μm and approximately 100 μm.

16. An apparatus configured to perform a method as claimed in claim 12 and having a processor configured to perform the calculating step.

17. An apparatus for inspecting the mounting of an electronic component on a substrate, the apparatus comprising:
a table for supporting a substrate, in use;
a line scan laser measurement sensor;
a positioning device configured to position the sensor laterally or horizontally offset from the table and oriented so as to project, in use, a laser line onto the substrate supported on the table, the laser line being inclined at a predetermined angle relative to the substrate such that a portion of the line is projected onto a region of the substrate disposed underneath an electrical component mounted on the substrate and a portion of the line is projected onto a region of the surface of the electrical component;
wherein the sensor is configured to measure a first distance from the sensor to at least one first point on the region of the surface of the electronic component by detection of backscattered light from the first point and is configured to measure a second distance from the sensor to at least one second point on the region of the substrate disposed underneath the electronic component by detection of backscattered light from the second point; and
a processor device configured to calculate the height of the electronic component above the substrate in dependence on the difference between the relative positions of points on the electronic component and/or the substrate and an angle of tilt of the sensor.

18. An apparatus as claimed in claim 17 wherein the positioning device comprises:
an X-Y Cartesian robot; and/or
the arcuate guide.

19. An apparatus as claimed in claim 17 comprising a rotation device configured to rotate the sensor relative to the electronic component about a substantially vertical axis.

20. An apparatus as claimed in claim 19, wherein the rotation device is arranged to rotate the arcuate guide relative to the electronic component about a substantially vertical axis.

* * * * *